United States Patent [19]
Nita et al.

[11] Patent Number: 5,342,292
[45] Date of Patent: Aug. 30, 1994

[54] ULTRASONIC ABLATION DEVICE ADAPTED FOR GUIDEWIRE PASSAGE

[75] Inventors: Henry Nita, Lake Forest; Russell Pflueger, Laguna Niguel, both of Calif.

[73] Assignee: Baxter International Inc., Deerfield, Ill.

[21] Appl. No.: 67,246

[22] Filed: May 24, 1993

Related U.S. Application Data

[63] Continuation of Ser. No. 787,292, Nov. 4, 1991, abandoned.

[51] Int. Cl.⁵ .............................................. A61B 17/20
[52] U.S. Cl. .................................... 604/22; 606/169
[58] Field of Search ............ 128/24 AA, 657; 604/22, 604/49, 52, 53; 606/159, 169, 171

[56] References Cited

U.S. PATENT DOCUMENTS

| | | |
|---|---|---|
| 4,750,902 | 6/1988 | Wuchinich et al. . |
| 3,352,303 | 11/1967 | Delaney . |
| 3,433,226 | 7/1968 | Boyd .................................. 128/305 |
| 3,526,219 | 9/1970 | Balamuth . |
| 3,565,062 | 2/1971 | Kuris .................................. 606/159 |
| 3,589,363 | 6/1971 | Banko . |
| 3,618,594 | 11/1971 | Banko . |
| 3,823,717 | 7/1974 | Pohlman ............................ 128/305 |
| 3,861,391 | 1/1975 | Antonevich et al. . |
| 3,896,811 | 7/1975 | Storz . |
| 4,188,952 | 2/1980 | Loschilov et al. . |
| 4,214,586 | 7/1980 | Mericle . |
| 4,223,676 | 9/1980 | Wuchinich et al. ................. 604/22 |
| 4,366,819 | 1/1983 | Kaster . |
| 4,431,006 | 2/1984 | Trimmer et al. . |
| 4,587,958 | 5/1986 | Noguchi et al. . |
| 4,587,972 | 5/1986 | Morantte ............................ 126/660 |
| 4,589,419 | 5/1986 | Laughlin et al. .................... 128/663 |
| 4,665,906 | 5/1987 | Jervis . |
| 4,692,139 | 9/1987 | Stiles . |

(List continued on next page.)

FOREIGN PATENT DOCUMENTS

| | | |
|---|---|---|
| 189329 | 7/1986 | European Pat. Off. . |
| 293472 | 11/1986 | European Pat. Off. . |
| 208175 | 1/1987 | European Pat. Off. . |
| 234951 | 2/1987 | European Pat. Off. . |
| 316796 | 11/1988 | European Pat. Off. . |
| 347098 | 6/1989 | European Pat. Off. . |
| 315290 | 10/1989 | European Pat. Off. . |
| 443256 | 12/1990 | European Pat. Off. . |

(List continued on next page.)

OTHER PUBLICATIONS

Circulation, vol. 81, No. 2, Feb. 1990, "Application of a New Phased-Array Ultrasound Imaging Catheter in the Assessment of Vascular Dimensions", pp. 660–666.

Primary Examiner—C. Fred Rosenbaum
Assistant Examiner—Michael Rafa
Attorney, Agent, or Firm—Raymond Sun

[57] ABSTRACT

An ultrasonic ablation device for effecting ultrasonic ablation of intravascular obstructions such as plaque or thrombi. The ultrasonic ablation device has a) an elongate catheter body, b) a wave guide or ultrasound transmission wire extending through the elongate catheter body, and c) a distal head or probe member positioned at the distal end of the catheter body. A guidewire lumen or passageway extends longitudinally through the catheter body and a guidewire aperture or passageway extends through the distal head or probe such that a guidewire may be passed through the distal head or probe and through the catheter body. Also disclosed is an improved distal head or probe which may be incorporated in any elongate ultrasonic ablation device, the improvement comprising the formation of a concavity or indentation in the distal or frontal face of the distal head or probe to improve the cavitation created thereby.

43 Claims, 9 Drawing Sheets

U.S. PATENT DOCUMENTS

| | | | |
|---|---|---|---|
| 4,799,496 | 1/1989 | Hargreaves et al. | 128/657 |
| 4,800,876 | 1/1989 | Fox et al. | 128/303.1 |
| 4,808,153 | 2/1989 | Parisi | 128/305 |
| 4,821,731 | 4/1989 | Martinelli | 128/662 |
| 4,841,977 | 6/1989 | Griffith | 128/660 |
| 4,844,092 | 7/1989 | Rybell et al. | 128/657 |
| 4,870,953 | 10/1989 | DonMicheal | 128/24 |
| 4,898,575 | 2/1990 | Fischell et al. | |
| 4,917,097 | 4/1990 | Proudian et al. | |
| 4,919,133 | 4/1990 | Chiang | |
| 4,920,954 | 5/1990 | Alliger et al. | |
| 4,924,863 | 5/1990 | Sterzer | 128/303.1 |
| 4,936,281 | 6/1990 | Stasz | 128/660 |
| 4,957,111 | 9/1990 | Millar | 128/662 |
| 4,960,411 | 10/1990 | Buchbinder | 128/657 |
| 4,967,653 | 11/1990 | Hinz | |
| 4,967,753 | 11/1990 | Haase et al. | |
| 4,979,939 | 12/1990 | Shiber | 604/22 |
| 4,988,356 | 1/1991 | Critterden et al. | 128/657 |
| 5,058,570 | 10/1991 | Idemoto et al. | |
| 5,061,238 | 10/1991 | Shuler | |
| 5,069,664 | 12/1991 | Guess et al. | |
| 5,076,276 | 12/1991 | Sakurai et al. | |
| 5,100,423 | 3/1992 | Fearnot | 604/22 |

FOREIGN PATENT DOCUMENTS

| | | |
|---|---|---|
| 9102489 | 3/1991 | European Pat. Off. |
| 472368 | 2/1992 | European Pat. Off. |
| 2349120 | 4/1975 | Fed. Rep. of Germany |
| 2438648 | 2/1976 | Fed. Rep. of Germany |
| 2453126 | 2/1976 | Fed. Rep. of Germany |
| 2453058 | 5/1976 | Fed. Rep. of Germany |
| 2541919 | 3/1977 | Fed. Rep. of Germany |
| 2703486 | 12/1977 | Fed. Rep. of Germany |
| 8119209 | 1/1981 | Fed. Rep. of Germany |
| 3707567 | 9/1987 | Fed. Rep. of Germany |
| 3707921 | 9/1987 | Fed. Rep. of Germany |
| 3826414 | 2/1989 | Fed. Rep. of Germany |
| 3812836 | 4/1990 | Fed. Rep. of Germany |
| 2242733 | 1/1980 | France |
| 2641693 | 1/1989 | France |
| 2643272 | 8/1990 | France |
| 8905123 | 6/1989 | PCT Int'l Appl. |
| 1531659 | 7/1977 | U.S.S.R. |
| 2208138A | 3/1989 | United Kingdom |
| 2208138 | 3/1989 | United Kingdom |
| 2212267 | 7/1989 | United Kingdom |
| 2212267 | 7/1989 | United Kingdom |
| WO87/01276 | 3/1987 | World Int. Prop. O. |
| WO87/05793 | 10/1987 | World Int. Prop. O. |
| 8906515 | 7/1989 | World Int. Prop. O. |
| 8907419 | 8/1989 | World Int. Prop. O. |
| 9001300 | 2/1990 | World Int. Prop. O. |
| WO90/07303 | 7/1990 | World Int. Prop. O. |
| WO91/14401 | 10/1991 | World Int. Prop. O. |

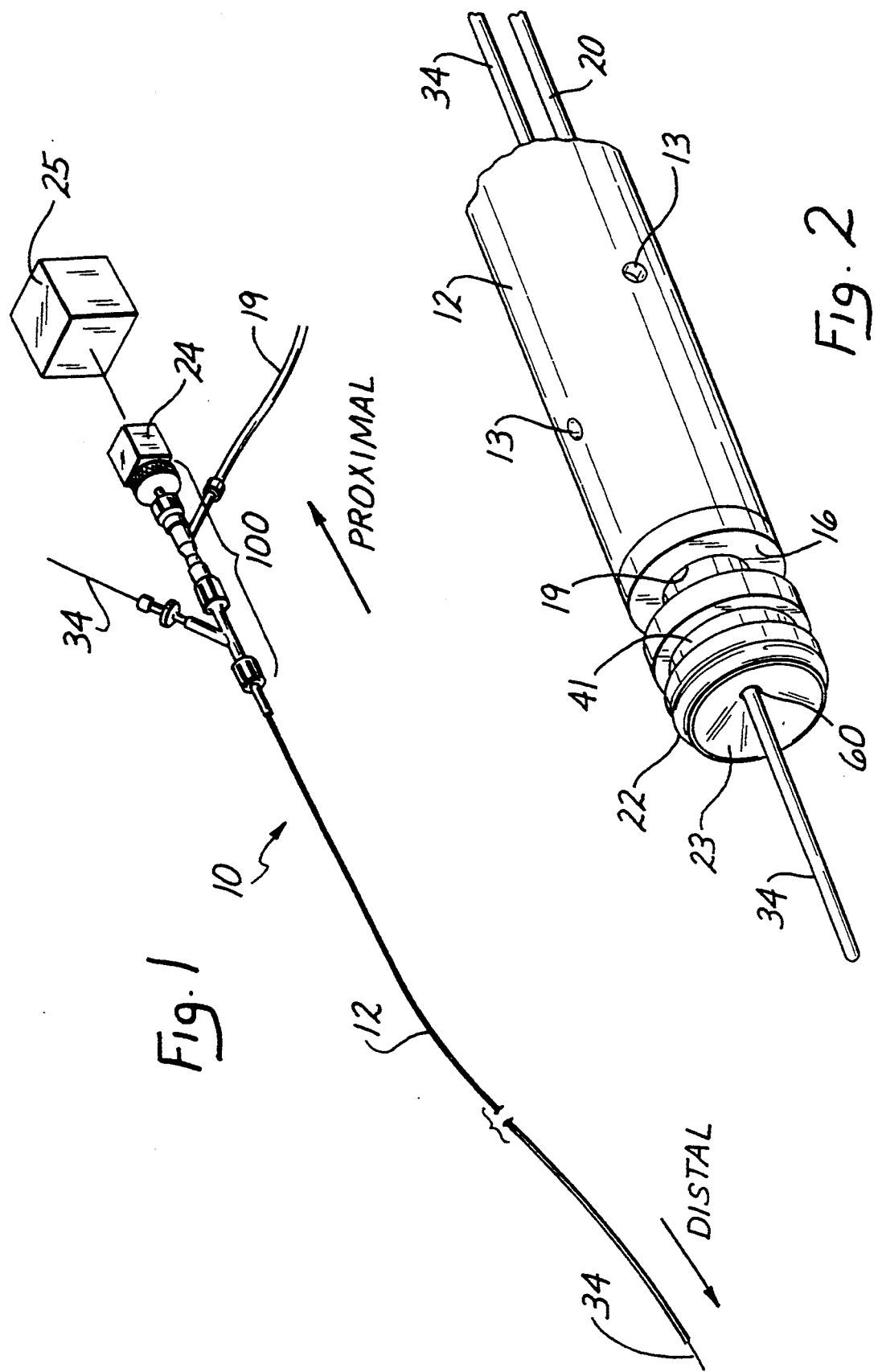

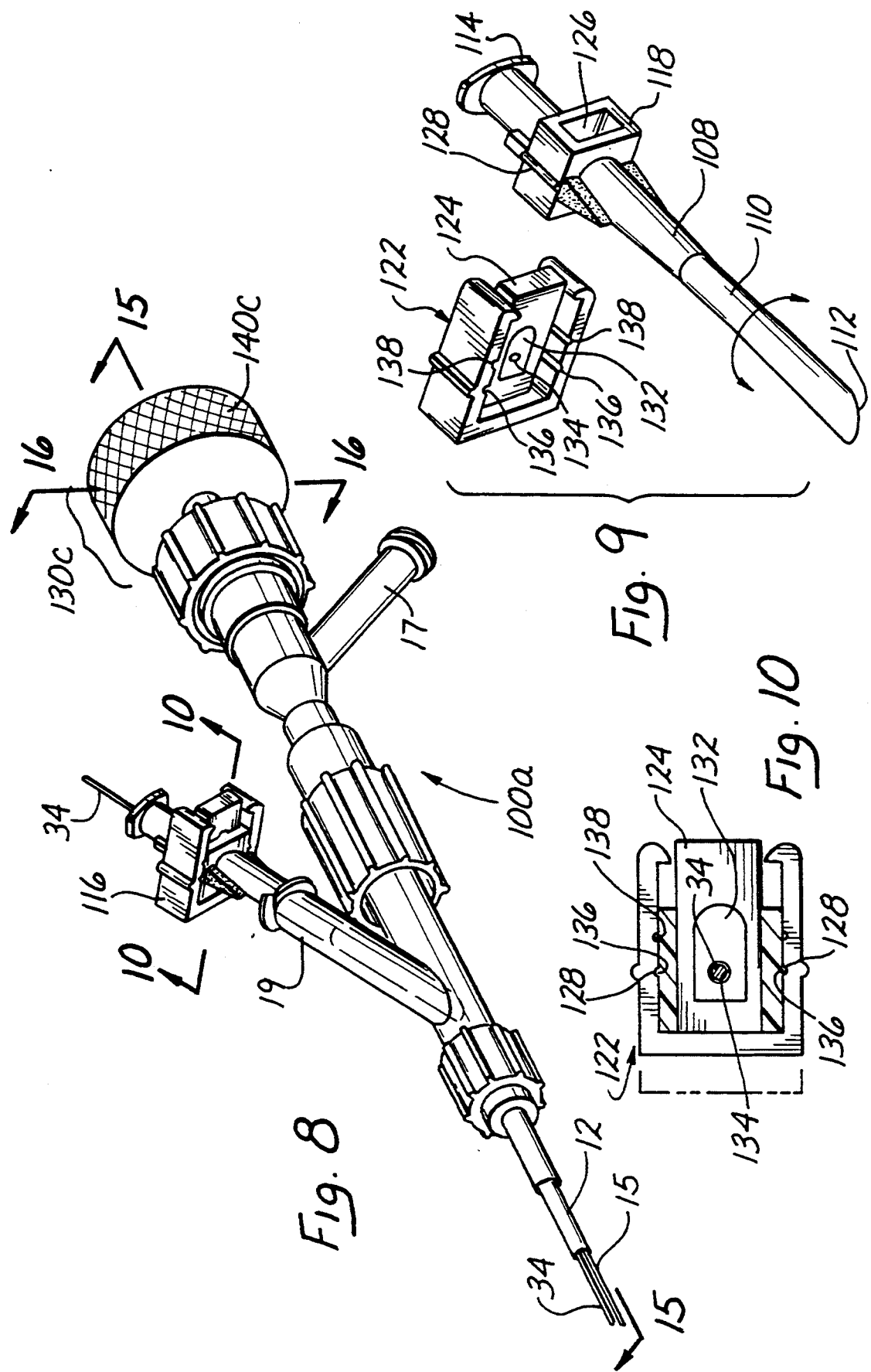

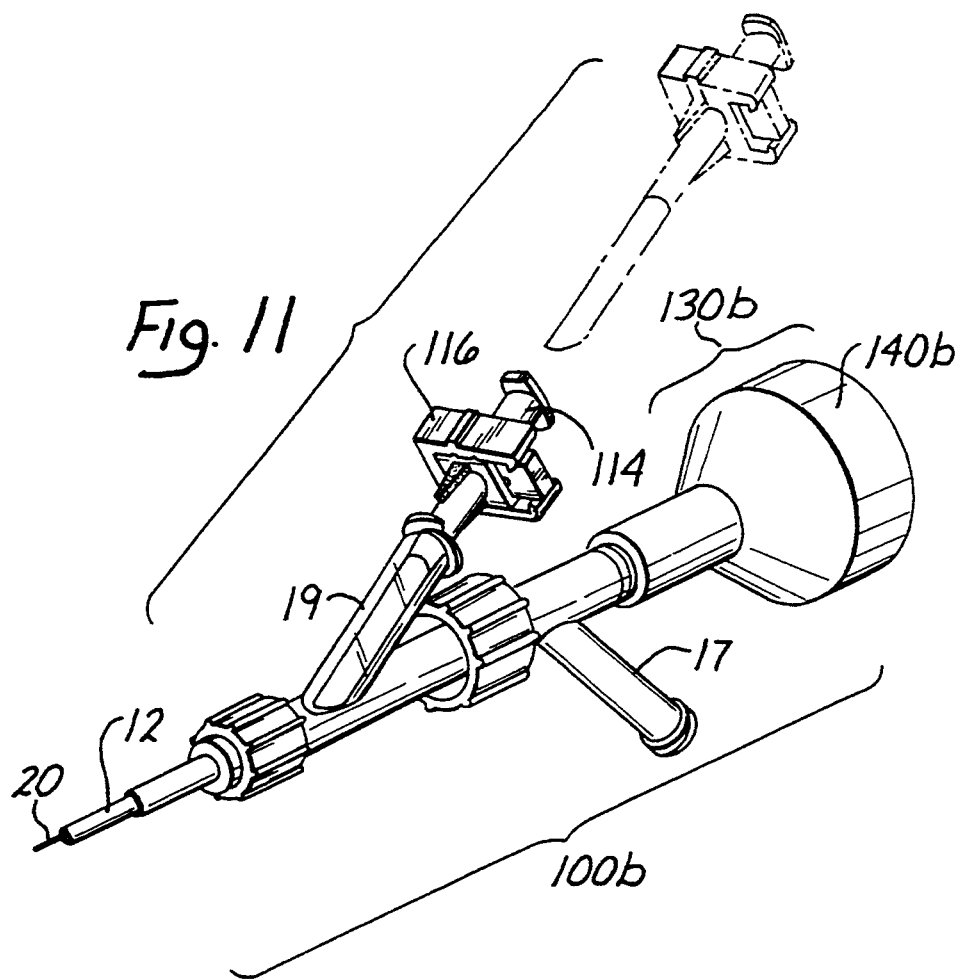
Fig. 11
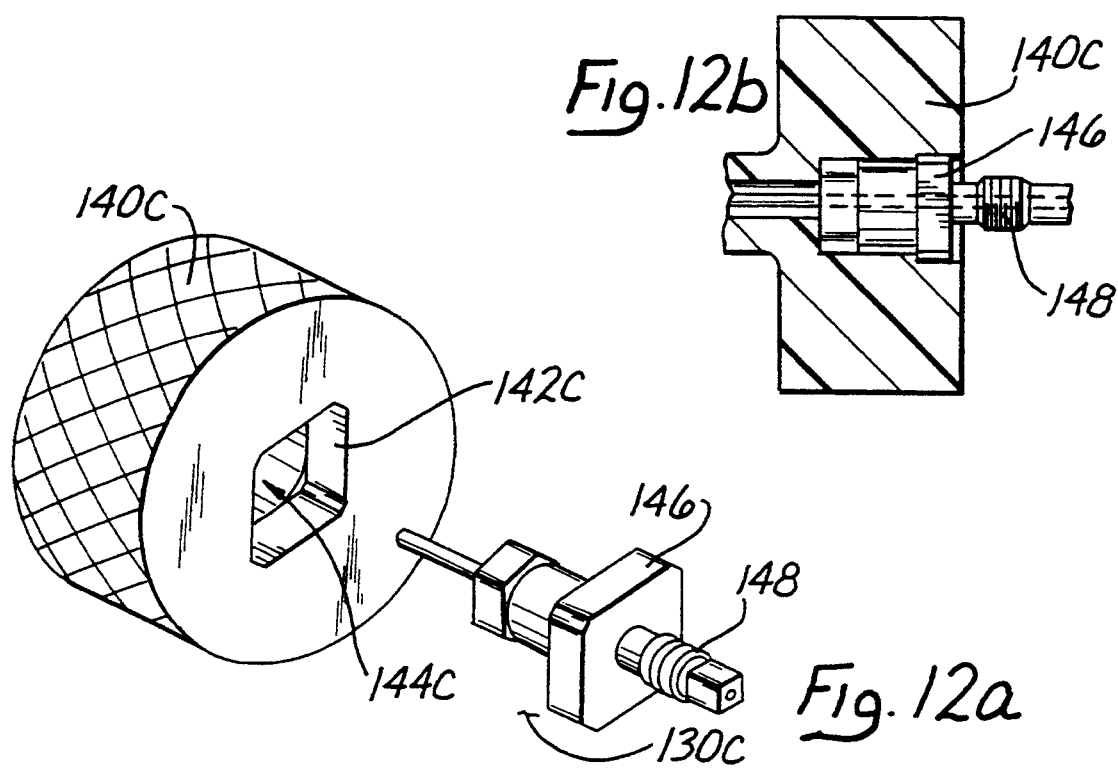
Fig. 12b
Fig. 12a

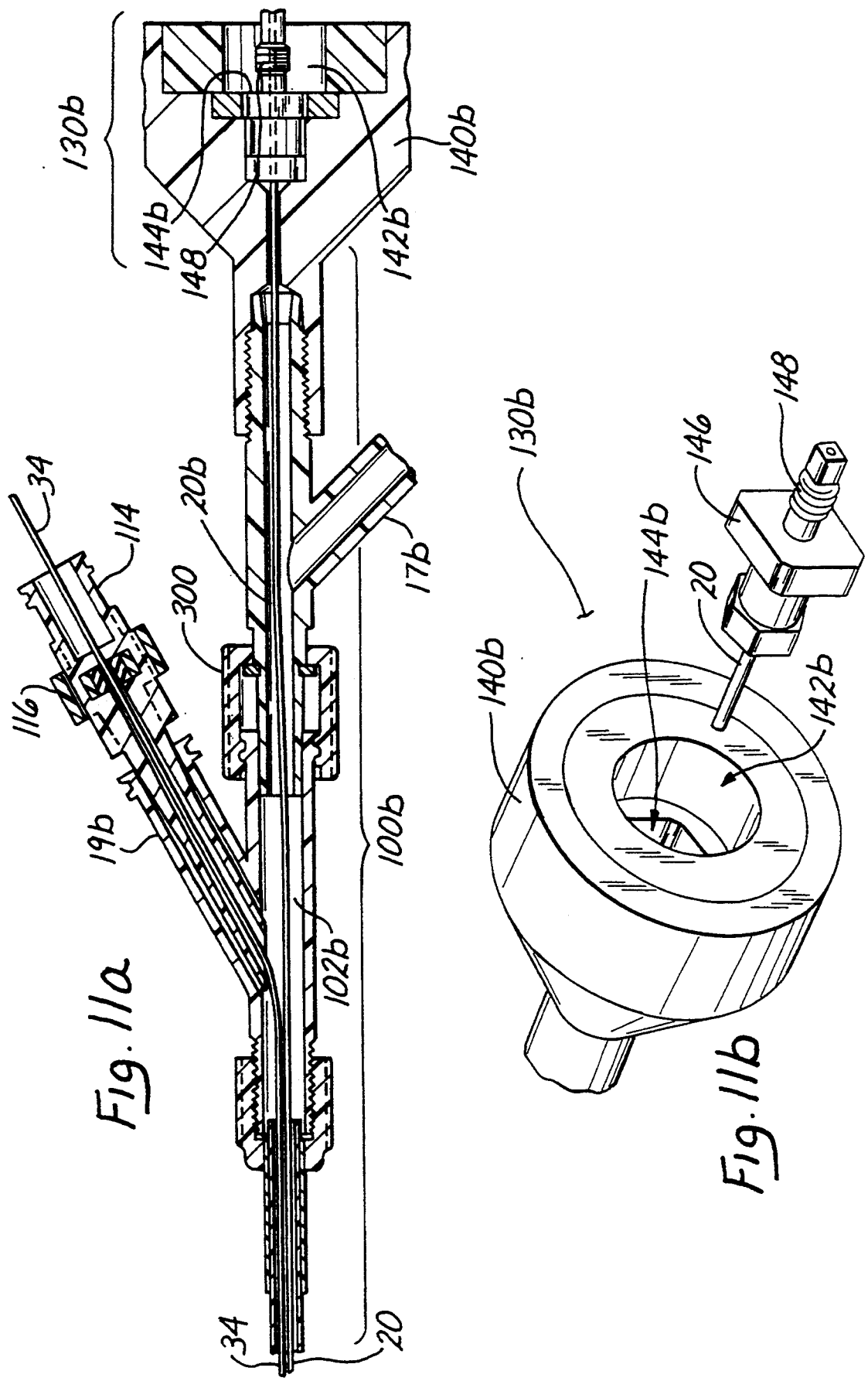

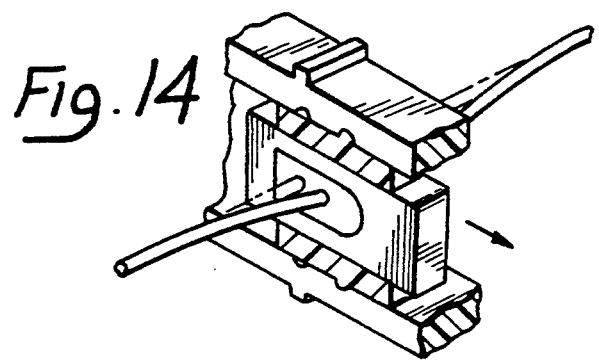
Fig. 14
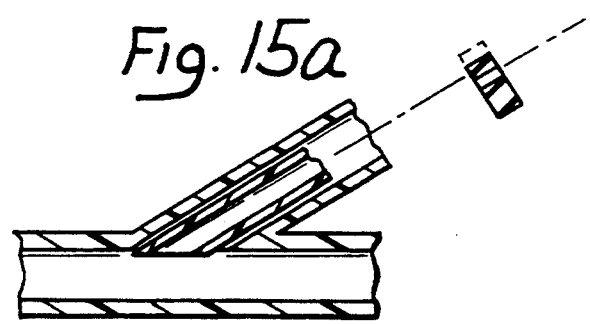
Fig. 15a
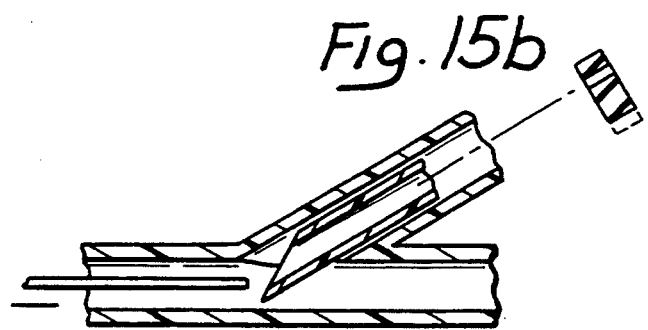
Fig. 15b
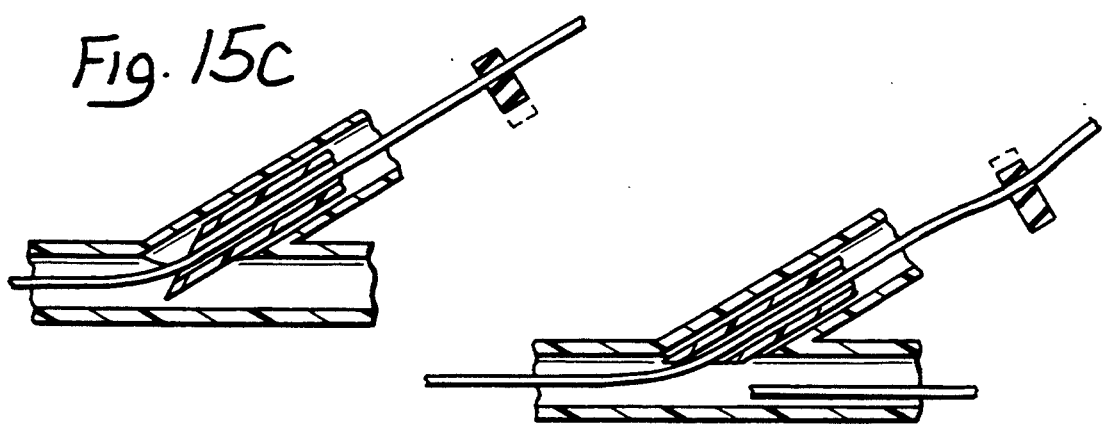
Fig. 15c
Fig. 15d
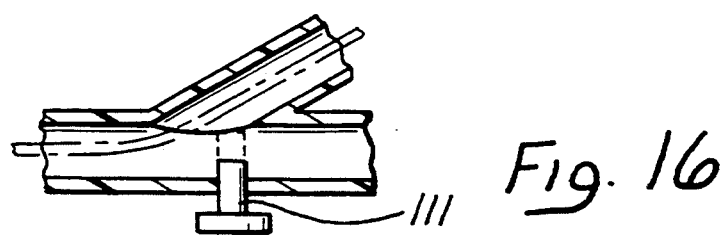
Fig. 16

ULTRASONIC ABLATION DEVICE ADAPTED FOR GUIDEWIRE PASSAGE

This is a continuation of application Ser. No. 07/787,292 filed on 4 Nov. 1991, abandoned.

FIELD OF THE INVENTION

The present invention pertains to medical equipment and more particularly to an improved ultrasonic ablation device for effecting ultrasonic ablation of intravascular obstructions.

RELATED CASES

This application is a continuation-in-part of co-pending U.S. patent application Ser. No. 07/640,190 U.S. Pat. No. 5,304,115 entitled "ULTRASONIC ABLATION DEVICE INCORPORATING IMPROVED TRANSMISSION MEMBER AND ABLATION PROBE", the entire written disclosure and drawings of which are expressly incorporated herein by reference.

BACKGROUND OF THE INVENTION

The use of ultrasonic energy to ablate obstructions within blood vessels has been proposed as a viable alternative to the commonly performed "balloon" angioplasty procedures wherein the occlusive lesion is dilated or compressed by inflation of a transluminally inserted balloon. Ultrasonic ablation may also be used to ablate thrombus within blood vessels.

Methods and apparatus for effecting ultrasonic ablation have been described in the prior art. One type of ultrasonic ablation apparatus known in the prior art comprises a flexible intravascular catheter having an ultrasound transmission wire or waveguide which extends longitudinally therethrough. A probe tip or distal head is formed on the distal end of the ultrasound transmission wire or waveguide. Such probe or distal head may protrude beyond the distal tip of the catheter. The proximal end of the transmission wire or waveguide is connected to an ultrasound generator. Sonic energy is thereby transmitted through the transmission wire causing the distal head or probe of the device to undergo vibratory movement. Such vibratory movement of the distal head or probe has been demonstrated to cause ablation of vaso-occlusive atherosclerotic lesions without damaging or perforating the surrounding blood vessel wall.

Examples of ultrasonic ablation devices and related apparatus used in the performance of ultrasonic angioplasty devices include those described in U.S. Pat. Nos. 3,433,226 (Boyd), 3,823,717 (Pohlman et al.), 4,808,153 (Parisi), 4,936,281 (Stasz), 3,565,062 (Kuris), 4,924,863 (Sterzer), 4,870,953 (DonMichael et al.); and other Patent Publications WO87-05739 (Cooper), WO89-06515 (Bernstein et al.), WO90-0130, (Sonic Needle Corp.); EP 316,789 (DonMichael, et al.); DE 3,812,836 (Schubert) and DE 2,438,648 (Pohlman).

The efficacy of any intravascular ultrasonic ablation procedure is inherently dependent upon the ability of the operator to position the ultrasonic ablation device in close spaced relation to occlusive plaque or thrombus so that the ultrasonic energy of the device may successfully ablate the occlusive plaque or thrombus.

One means of facilitating proper advancement and positioning of the ultrasound ablation device or catheter is to initially insert and advance a flexible, radiographically visible, guidewire through the vasculature to a point where the distal tip of such guidewire is immediately adjacent, or actually passing through, the offending plaque or thrombus. Thereafter, the ultrasonic ablation catheter or device may be threaded over the prepositioned guidewire to a point where the therapeutic tip or head of the ultrasound catheter is adjacent or in contact with the occlusive plaque or thrombus. Alternatively, prior to insertion of either the guidewire or the ultrasound catheter, the ultrasound catheter may be advanced over the guidewire such that the distal tip of the guidewire extends slightly out of and beyond the distal end of the catheter. Thereafter, the ultrasound ablation catheter and guidewire may be inserted and advanced together through the vasculature to a point at or near the occlusive plaque or thrombus. Thereafter, the guidewire may be further advanced relative to the ultrasound catheter so as to penetrate or pass through the occlusive plaque or thrombus. Thereafter, the ultrasound catheter may be advanced relative to the guidewire to affect the desired ablation of such occlusive plaque or thrombus.

After the ultrasound catheter has been utilized to ablate the occlusive plaque or thrombus, it may be desirable to extract and remove the previously inserted guidewire. In some cases, it may thereafter be desirable to reinsert the same guidewire or a different guidewire through the ultrasound catheter without requiring retraction or removal of the ultrasound catheter.

In view of the desirability of using an ultrasound catheter in conjunction with a prepositioned guidewire, there exists a need in the art for improved or alternative ultrasonic angioplasty catheter devices which are specifically designed and configured for use with a guidewire. In some situations, it may be desirable to fully extract and remove the guidewire from the catheter after the catheter has been advanced to its operative position at the site of the occlusion. To facilitate such extraction and removal of the guidewire, it is desirable that the distal portion of the guidewire be exteriorized in such a manner as to allow the operator to fully extract or insert a guidewire through the ultrasound catheter.

SUMMARY OF THE INVENTION

The present invention overcomes some or all of the shortcomings of the prior art by providing an ultrasound catheter having a distal end opening or aperture and a guidewire passageway or lumen extending therethrough to permit slidable passage of a flexible guidewire through said ultrasound catheter.

In accordance with the invention, there is provided an ultrasound catheter comprising (a) an elongate flexible catheter having a proximal end, a distal end and at least one lumen extending longitudinally therethrough; (b) an ultrasound transmission member or wave guide which extends longitudinally through a lumen of the flexible catheter; (c) a distal head or probe attached to or formed on the distal end of the transmission member or wave guide; and (d) an aperture or bore formed through the distal head or probe to permit slidable passage of a flexible guidewire through the distal head or probe and through a lumen of the flexible catheter.

Further in accordance with the invention, there is provided a proximal end connector assembly mountable on the proximal end of an ultrasound catheter for connecting the ultrasound transmission member of the device to an ultrasound generator and for facilitating insertion/extraction of the flexible guidewire. The proximal end connector may also be adapted to receive infusion of coolant fluid to minimize the build-up of heat within the ultrasonic device. Such proximal end connector assembly may comprise: (a) a hollow body member having a hollow inner bore in fluid communication and/or alignment with the lumen of the ultrasound catheter; (b) a side opening, sidearm, aperture or other opening or means for a allowing a guidewire to pass into or out of the hollow inner bore of the body member and (c) a diverter member insertable or deployable into the inner bore of the proximal end connector to divert the leading tip of a proximally advanced guidewire from the inner bore of the proximal connector, outwardly through the sidearm thereof.

Still further in accordance with the invention, there is provided a method of performing ultrasound ablation of an intravascular occlusion whereby an elongate flexible guidewire having a proximal end and a distal end is inserted, distal end first, into the vasculature and advanced to a point where the distal end of the guidewire is adjacent or beyond an intravascular obstruction to be treated. Thereafter, the proximal end of the guidewire is inserted through an aperture or passageway formed in the distal head or probe of the ultrasound catheter and the guidewire is advanced into an inner lumen thereof. After the proximal end of the guidewire has been inserted through the distal head of the ultrasound catheter and into the lumen thereof, the ultrasound catheter is then advanced distally over the guidewire to a point where the distal head or probe of the ultrasound catheter is operatively positioned in relation to the lesion. As the ultrasound catheter is advanced distally over the guidewire, the proximal end of the guidewire may be diverted through a sidearm or other opening so as to pass outwardly from the lumen of the ultrasound catheter, thereby causing the proximal end of the guidewire to be fully exteriorized and readily graspable and manipulatable by the hand of the operator. Thereafter, the operator may grasp the exteriorized proximal end of the guidewire to manipulate the guidewire and may thereby extract the guidewire fully from the lumen of the angioplasty catheter.

Still further in accordance with the invention, there is provided an alternative method of performing ultrasound ablation of an intravascular occlusion whereby a guidewire of the foregoing character is pre-inserted or pre-loaded within the guidewire lumen of the ultrasound catheter such that a short portion of the guidewire extends out of and beyond the guidewire aperture or passageway formed in the distal head of the ultrasound catheter. The ultrasound catheter and pre-inserted guidewire are then concomitantly inserted into and advanced through the vasculature to a point adjacent the occlusion or thrombus to be treated. Thereafter, the guidewire may be advanced in a distal direction such that the distal end of the guidewire will pass through and cross the occlusion. Thereafter, the ultrasound catheter may be further advanced in the distal direction over the guidewire so as to effect ablative treatment of the occlusion. Thereafter, the guidewire and ultrasound catheter may be concomitantly or separately extracted, withdrawn and removed from the body.

Still further in accordance with the invention, there is provided an improved distal head configuration for an ultrasonic ablation device or ultrasonic catheter wherein said distal head has a distal or frontal surface in which at least one concavity is formed. Such concavity may be in the form of a rounded depression, conical depression, frusto-conical depression or other configuration. The formation of such concavity in the frontal surface of the distal head serves to improve the cavitation created by the ultrasonic ablation device in a fluid environment.

Further objects and advantages of the invention will become apparent to those skilled in the art upon reading and understanding the following detailed description and the accompanying drawings.

BRIEF DESCRIPTION OF THE DRAWINGS

FIG. 1 is a perspective view of an ultrasound catheter of the present invention having a flexible guidewire extending therethrough.

FIG. 2 is a cut-away perspective view of the distal end portion of the ultrasound catheter shown in FIG. 1.

FIG. 8 is a perspective view of a first embodiment of a proximal connection apparatus which forms a portion of an ultrasound catheter of the present invention.

FIG. 9 is an exploded view of a preferred guidewire diverter apparatus which may incorporated into the ultrasound catheter of the present invention.

FIG. 10 is a cross-sectional view through line 10-10 of FIG. 8

FIG. 11 is a perspective view of an alternative embodiment of a proximal connector assembly which may be incorporated into the ultrasound catheter of the present invention.

FIG. 11a is a longitudinal sectional view of the alternative embodiment of the proximal end connector assembly shown in FIG. 11.

FIG. 11b is an exploded rear perspective view of the sonic connector positioned on the proximal end of the proximal connector assembly shown in FIG. 11a.

FIG. 12a is a rear perspective view of an alternative sonic connector assembly which may be incorporated in the ultrasound catheter of the present invention.

FIG. 12b is a longitudinal sectional view of the sonic connector assembly shown in FIG. 12a.

FIG. 13b is a longitudinal sectional view of the sonic connector assembly shown in FIG. 13a.

FIG. 14 is a perspective view of a guidewire anchoring apparatus which may be incorporated into the ultrasound catheter of the present invention.

FIGS. 15a–15d are longitudinal sectional illustrations of a portion of the ultrasound catheter of the present invention showing, step-by-step, the advancement of the device over a prepositioned guidewire.

FIG. 16 is a longitudinal sectional view of an alternative proximal connection apparatus which forms a portion of an ultrasound catheter of the present invention and which incorporates an alternative guidewire diverter means for diverting the proximal end of a guidewire out of the device.

DETAILED DESCRIPTION OF THE PREFERRED EMBODIMENT

The following detailed description and the accompanying drawings are provided for purposes of illustrating and describing presently preferred embodiments of the invention and not for the purpose of limiting the invention in any way.

Figure 5:
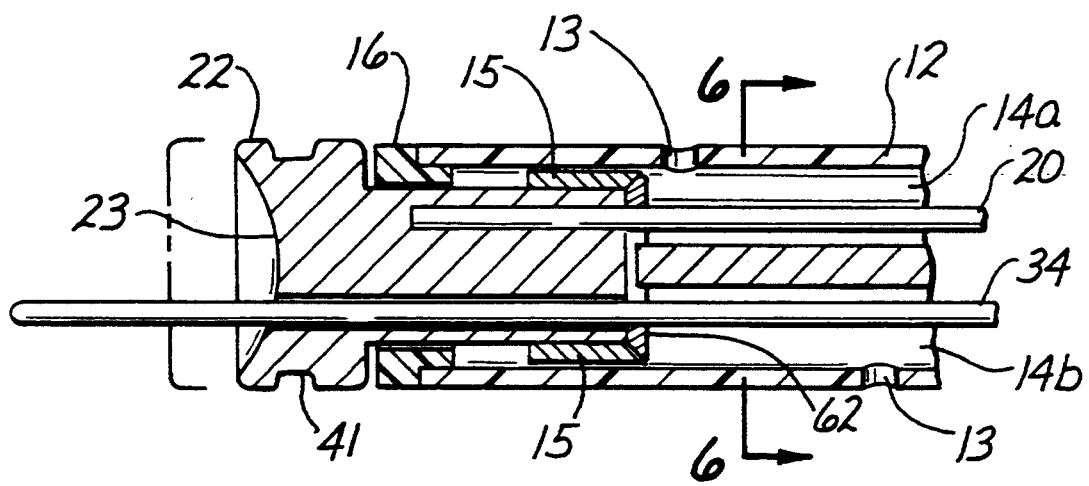
FIG. 5 is a longitudinal sectional view of the distal tip portion of an alternative 2-lumen embodiment of an ultrasound catheter of the present invention.

As shown in the drawings, one embodiment of the ultrasound catheter 10 of the present invention comprises an elongate flexible catheter body 12 having a distal end and a proximal end. At least one hollow lumen 14 extends longitudinally through the flexible catheter body 12. An ultrasound transmission member or wire 20 extends longitudinally through the lumen 14. A distal head or probe 22 is mounted on the distal end of the catheter body 12 and is connected to the ultrasound transmission member or wire 20 such that the transmission of sonic energy through the ultrasound transmission member or wire 20 will cause the distal head or probe 22 to vibrate. The distal head or probe 22 may be formed in many different configurations. The particular configuration of the distal head or probe 22 shown in the drawings is that of a bulbous member having an optional annular groove or depression 41 extending therearound. Also, an optional concavity or depression is formed in the frontal or distal surface 23 of the distal head 22. Such concavity or depression formed in the frontal or distal surface 23 serves to facilitate cavitation when the ultrasonic device is operated within a fluid environment. The concavity or depression formed within the frontal or distal surface 23 of the distal head 22 may be of any suitable configuration such as a rounded depression as shown in FIG. 5 or a conical or frusto-conical depression, such as that shown in FIGS. 2 and 3. Various other configurations of depressions or concavities may also be formed in the frontal or distal surface 23 of the distal head 22 to improve and enhance the cavitation effects of the device. The formation of such concavity or depression in the frontal or distal surface 23 of the distal head 22 is an improvement which may be utilized on any ultrasound ablation device or ultrasonic catheter and is not limited to the embodiments shown herein or to ultrasound catheters having guidewire passage apertures as those shown in the drawings.

The proximal portion of the distal head 22 is slightly smaller in diameter than the inner diameter of the distal tip opening 19 of the catheter body 12. A stay member 15 is affixed to or formed on the proximal end of the distal head 22. The outer diameter of the stay member 15 is slightly smaller than the inner diameter of the adjacent inner wall of the catheter body 12, thereby providing a small space between the outer surface of the stay member 15 and the adjacent inner wall of the catheter body 12. The stay member 15 is sized, configured and positioned so as to abut against abutment shoulder 21 upon distal advancement of the distal head 22 relative to the catheter body 12. Thus, the distal head 22 remains free to vibrate back and forth within the catheter body but is deterred or prevented from being fully extracted from the catheter body by abutment of the stay member 15 against the abutment shoulder 21 formed within the distal tip 16 of the catheter body 12.

The ultrasound transmission member 20 inserts into a cylindrical bore 50 which extends partially through the distal head 22. It is preferable that the distal end of the ultrasound transmission member or wire 20 be press-fit into the cylindrical bore 50 such that the ultrasound transmission member 20 will remain frictionally held therein. Such press-fitting of the ultrasound transmission member 20 into the cylindrical bore 50 may be accomplished by mechanically forcing the distal end of the ultrasound transmission member into the cylindrical bore 50. Another means of accomplishing such press-fit frictional retention of the ultrasound transmission 20 within the cylindrical bore 50 is to initially warm the distal head 22 to cause expansion and diametric enlargement of the cylindrical bore 50 sufficient to permit insertion of the distal end of the ultrasound transmission member 20 thereinto. After the ultrasound transmission member 20 has been inserted into the cylindrical bore, the distal head is cooled to ambient temperature, thereby allowing the cylindrical bore 50 to return to its original non-expanded size whereby the cylindrical bore will firmly frictionally engage and hold the distal end of the ultrasound transmission member 20. Depending on the metal or metal alloy of which the ultrasound transmission member is formed, it may be desirable to avoid the use of welding or other high temperature processes as exposure of the ultrasound transmission member 20 to extreme temperatures may result in changes in the crystal and structure and/or resultant weakening of the ultrasound transmission member 20 at the site of such welding or extreme-temperature process.

Fluid outflow ports 13 are formed in the sidewall of catheter body 12 to permit flow of coolant liquid through lumen(s) 14. Coolant fluid may thus be infused from the proximal end of the catheter body, through the lumen of the catheter and out of fluid outflow ports 13 and guidewire passageway 60, 60a, thereby providing a flow of coolant liquid over the ultrasound transmission member or wire 20 to prevent overheating during use.

Figure 3:
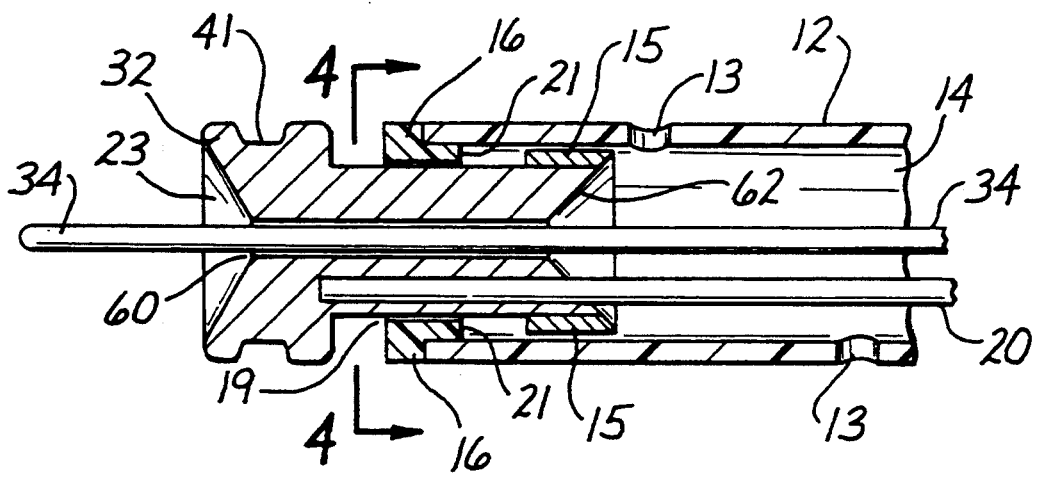
FIG. 3 is a longitudinal sectional view of the portion of the device shown in FIG. 2.

A guidewire passage aperture is formed longitudinally through the distal head 22. Such guidewire passage aperture 60 may be formed in the center of the distal head 22 as shown in FIG. 3 or may be positioned eccentrically as shown in FIG. 5. A chamfered or outwardly bevelled enlargement 62 may be formed on the proximal end of the guidewire passage aperture 60 or 60a. Such chamfered or outwardly bevelled enlargement 62 is provided to guide and facilitate passage of the distal end of guidewire 34 into the proximal end of guidewire passage aperture 60 or 60a. The diameter of the chamfered enlargement 62 is preferably sufficiently large in relation to the inner diameter of the catheter body 12 to consistently receive the distal tip of a flexible guidewire 34 being freely advanced through the lumen 14 of the catheter body 12. Such sizing of the chamfered enlargement 62 enables the leading distal tip of the guidewire 34 to be captured and passed into and through the guidewire aperture 60 or 60a with minimal need for aiming more specific positioning of the guidewire 34 within the lumen 14 of the catheter 12.

Figure 4:
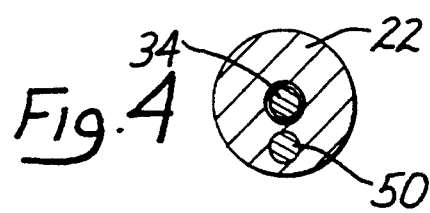
FIG. 4 is a cross-sectional view through line 4—4 of FIG. 3.

In the embodiments shown in FIGS. 3 and 4, the catheter body 12 comprises a single lumen 14. Both the ultrasound transmission member 20 and the flexible guidewire 34 extend through the common single lumen 14.

Figure 6:
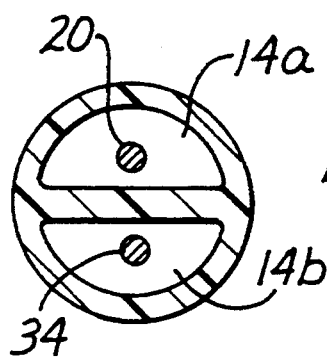
FIG. 6 is a cross-sectional view through line 6—6 of FIG. 5.
Figure 7:
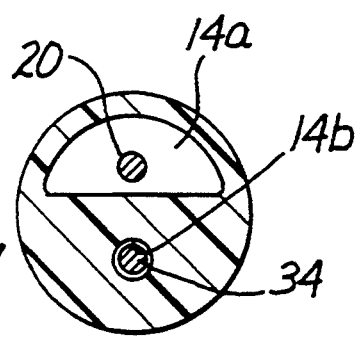
FIG. 7 is a cross-sectional view showing an alternative 2-lumen embodiment of an ultrasound catheter of the present invention wherein one lumen is larger than the other lumen.

In the embodiments shown in FIGS. 5–7, the catheter body comprises separate lumens 14a and 14b wherein the ultrasound transmission member 20 and flexible guidewire 34 with the ultrasound transmission member 20 being positioned in one such lumen 14a and the flexible guidewire 34 being insertable/retractable through the other such lumen 14b.

A proximal end connection assembly or apparatus 100 may be positioned on the proximal end of the catheter body 12 to facilitate operative connection of the ultrasound transmission member 20 to an attendant ultrasound generating device 24 and/or to facilitate (a) insertion/extraction of the flexible guidewire 34 and/or (b) infusion or withdrawal of fluids through the lumen 14 of the catheter body 12.

Preferably, the proximal connection apparatus 100 is attached to the proximal end of the catheter body 12 such that the ultrasound transmission member 20 may extend directly through the proximal connection apparatus and such that it may be attached to an attendant ultrasound generator 24.

The proximal connection apparatus 100 may comprise a rigid outer body defining a hollow bore 102 or inner chamber which extends longitudinally therethrough. The proximal connection apparatus 100 is mounted on the proximal end of the catheter body 12 such that the hollow bore 102 or inner chamber is in continuous alignment with and fluidly connected to, the lumen 14 of the catheter body 12. A sonic connector assembly 130 is mounted on the proximal end of the proximal connection apparatus 100. The sonic connector assembly 130 operates to facilitate connection of the ultrasonic transmission member or wire to a separate ultrasound transducer (or ultrasound generating device). The sonic connector assembly may be formed in numerous configurations, several of which are more fully described herebelow and shown in FIGS. 8, 8a, 11, 11a, 11b, 12a, 12b, 13a and 13b.

A fluid infusion sidearm 17 is provided to permit fluid to be infused into or withdrawn from the inner bore or chamber 102. Sidearm 17 is typically utilized to infuse a distally directed flow of coolant liquid through the inner bore or chamber 102, through the lumen 14 of the catheter body 12, and out of the ports 13 located at or near the distal end of the catheter body 12 and through guidewire passageway 60, 60a. Such infusion of coolant liquid serves to remove heat from the ultrasound transmission member 20 and prevents overheating thereof.

A guidewire passage sidearm 19 may also be mounted on the rigid body of the proximal connector apparatus 100. The flexible guidewire 34 is insertable through and/or withdrawable from guidewire passage sidearm 19. In some applications, the flexible guidewire 34 will be inserted into the vasculature prior to deployment of the ultrasound catheter. After the guidewire has been advanced to a position where the distal tip of the guidewire is within and/or adjacent the lesion to be treated, the exteriorized proximal end of the guidewire 34 is inserted into the guidewire passage aperture 60 of the distal head 22 of the ultrasound catheter. The ultrasound catheter may then be advanced in a distal direction over the pre-positioned guidewire to a point where the proximal end of the guidewire 34 emerges from the proximal end of the catheter body 12 and into the inner bore 102 of the proximal end connector apparatus 100. A diverter member 108 may be inserted through sidearm 19 as the ultrasound catheter is advanced in a distal direction through bore 102 to cause the proximal end of the guidewire 34 to be diverted from bore 102 into the lumen of sidearm 19 such that the proximal end of the guidewire 34 will emerge out of sidearm 19.

One preferred diverter member 108 comprises a cylindrical tubular forebody 110 having a hollow lumen extending therethrough and a bevelled tip 112. A leur lock adaptor 114 is formed on one end of the forebody 110 as shown. A guidewire gripping or locking apparatus 116 is formed or mounted between the tubular forebody 110 and the leur lock 114. One embodiment of a guidewire gripping or locking apparatus 116 which is usable for this purpose is commercially available (Baxter Healthcare Corporation, Irvine, Calif. 92714). The guidewire gripping or locking apparatus 116a comprises a hollow portion through which the tubular lumen of the diverter member 108 passes. A rectangular slot or aperture 120 extends through the hollow portion 118. A slidable locking member 122 comprises a U-shaped outer body having a central tongue or projection 124. The central tongue or projection 124 is sized and configured to slidably insert into the aperture or passageway 120 of the hollow portion 118. An elastomeric insert 132 having an aperture 134 formed therein is positioned in the mid-region of the tongue member 124. A first set of registration grooves 136 and a second set of registration grooves 138 are formed on the inner faces of the U-shaped outer portion of the locking member 122. Ribs 128 are formed on the outer surfaces of the hollow portion 118, such ribs 128 being sized and configured to register and seat within the corresponding grooves 136 and 138. The first set of grooves 136 are positioned in relation to aperture 134 such that when the tongue portion 124 is inserted within aperture 120 and the locking member 122 is advanced to a point where the first set of grooves 136 are seated over ribs 128, the aperture 134 will be aligned with the lumen of the diverter member 108 such that a flexible guidewire may be advanced through aperture 134. Thereafter, the locking member 122 may be moved to a point where the ribs 128 become seated in the second set of grooves 138 such that the location of the aperture 134 will shift out of alignment with the lumen of the diverter member 108 and the guidewire will distort the elastomeric insert 132 in a lateral direction such that the elastomeric insert will substantially seal about the outer surface of the guidewire, thereby gripping and holding the guidewire in a substantially fixed position preventing back and forth movement of the guidewire 34. Such also forms a substantially fluid tight seal, thereby preventing backup of liquid past the locking member 118. If it is desired to release the guidewire to again allow forward and backward movement thereof, the locking member 122 may be returned to the first position whereat the first set of grooves 138 are seated on ribs 128, thereby once again returning the aperture 134 into alignment with the lumen of the diverter member 108 and once again allowing the guidewire to be slidably advanced or retracted at will.

In accordance with the step-by-step diagram shown in FIGS. 15a–15b, the diverter member 108 may be inserted into guidewire passage sidearm 19 to a position whereat the bevelled distal tip 112 of the diverter member 108 is flush with the upper wall of the inner bore 102 of the proximal connector apparatus. As the proximal end of the guidewire 34 approaches the guidewire passage sidearm 19, the diverter member 108 may be rotated causing the bevelled distal tip 112 to move downwardly to a position near and/or in abutment with the bottom wall of the inner bore 102. In such position, the advancing proximal end of the guidewire 34 will pass into the inner bore of the diverter member 108 and be thereby shunted or diverted outwardly through the inner bore of member 108 positioned within sidearm 19. As distal advancement of the ultrasound catheter continues, an increasingly larger portion of the guidewire 34 will extend out of and beyond the leur adaptor 114 of the diverter member 108. Such exteriorized portion of the guidewire 34 is directly accessible to the operator of the device and may be grasped by hand so as to allow the operator to manually withdraw, advance, rotate or otherwise manipulate the guidewire 34.

FIG. 16 shows one possible alternative embodiment to the insertable diverter member 108. In the embodiment shown in FIG. 16, an outwardly biased or spring loaded depressible obstructing or obturator 111 is formed or mounted in the wall of the proximal connector apparatus 120 directly adjacent the juncture between inner bore 102 and the hollow lumen of sidearm 19. Such obstructor member or obturator 111 may be depressed momentarily when the proximal end of the guidewire 34 reaches the juncture between sidearm 19 and the proximal portion of inner bore 102. Such depression of the obstruction member or obturator 111 will deter or prevent the guidewire from entering the proximal portion of inner bore 102 and, instead, will divert the guidewire into the lumen of sidearm 19. After such diversion is complete, the obstruction member or obturator 111 is released and allowed to return to its original position whereby it does not obstruct the inner bore 102 of the proximal connector apparatus 100.

Alternative embodiments of the proximal connector apparatus 100 are shown in FIGS. 8, 8a, 11, 11a, 14 and 17.

Figure 8A:
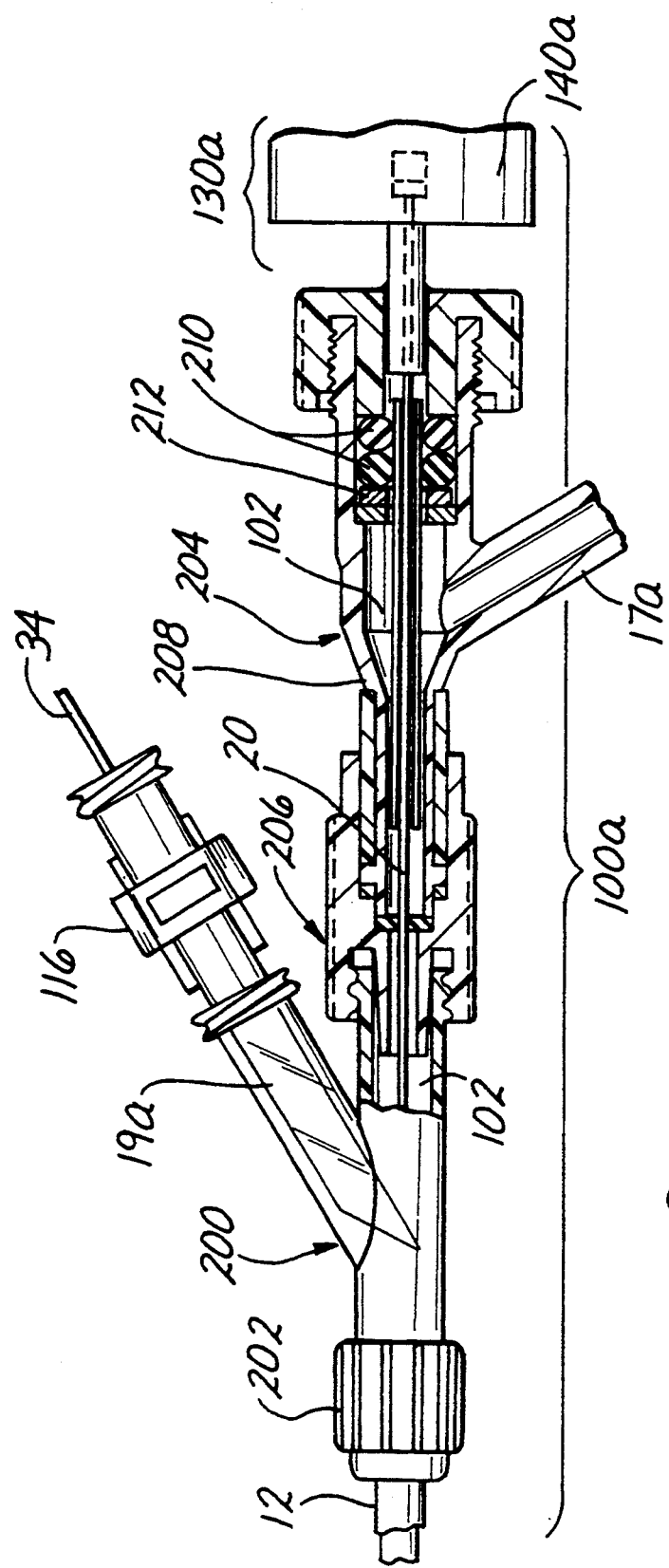
FIG. 8a is a longitudinal sectional view of the proximal connection apparatus shown in FIG. 8.
Figure 13A:
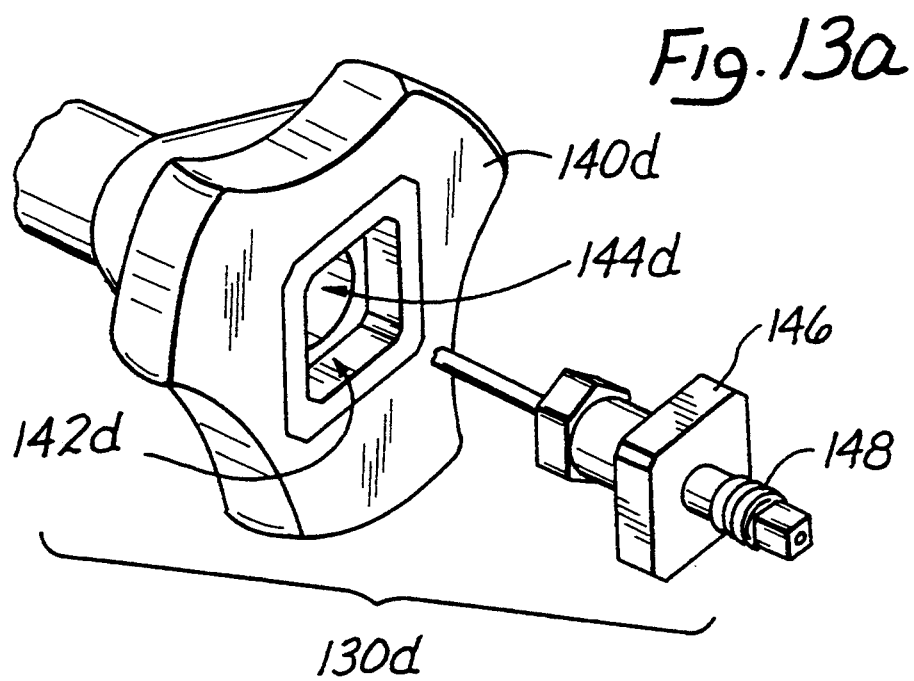
FIG. 13a is a rear perspective view of yet another alternative embodiment of a sonic connector assembly which may be incorporated into an ultrasound catheter of the present invention.
Figure 13B:
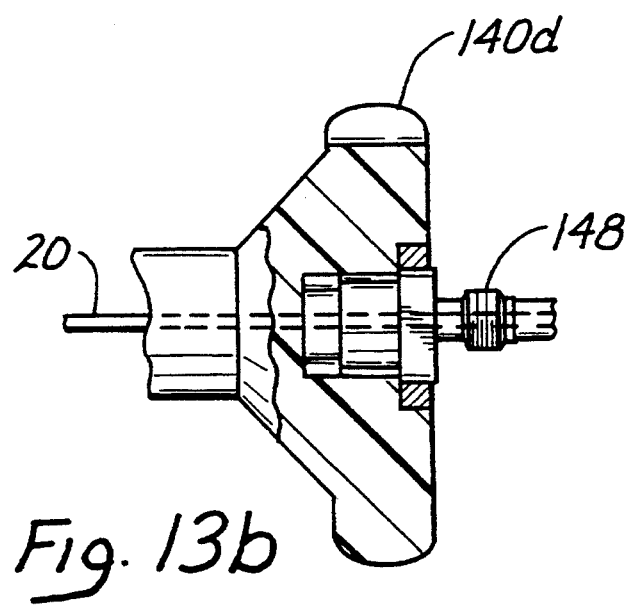

The embodiment 100a of FIGS. 8 and 8a is constructed such that the rigid body of the proximal connection apparatus 100a is formed of a forward or frontal portion 200 connectable to the catheter body 12 by way of a catheter connection fitting 202. A rear or proximal portion 204 is connected to the frontal portion 200 by way of a mid-connector portion 206. A plastic tube 208 is disposed around a portion of the ultrasound transmission member 20 within the bore 102 of the connector assembly 100a. The plastic tube 208 is preferably formed of material such as silicone. It is preferable that the inner diameter of the plastic 208 be slightly largely than the outer diameter of the ultrasound transmission member 20 such that a space exists therebetween. Dual O-rings 210 and washer 212 make direct contact with the outer surface of the tube 208 without exerting sufficient pressure to cause the tube 208 to collapse or compress inwardly in a manner that would cause the tube 208 to come into contact with or press against the ultrasound transmission member 20. By such arrangement, the tube 208 is held firmly in place by the surrounding O-rings 210 and/or washer 212 while sufficient space remains within the tube 208 around the ultrasound transmission member 20 to permit coolant fluid to flow from the inner bore 102 into the tube 208 so as to bathe and cool the portion of the ultrasound transmission member 20 which is disposed within tube 208. Tube 208 is preferably sized, configured, positioned and made of material which is sufficiently rigid to dampen or limit side-to-side whipping or lateral movement of the ultrasound transmission member 20.

The alternative embodiment 100b of the proximal connector apparatus 100 shown in FIG. 11 and 11a is formed in two separate sections joined by a threaded nut member 300. When joined by nut member 300, the front and rear sections of the alternative proximal connector apparatus 100b define a hollow inner bore 102b therethrough. Fluid infusion sidearm 17b and guidewire passage sidearm 19b each have hollow inner bores which are in fluidic connection with the inner bore 102b of the proximal connector 100b. The ultrasound transmission member 20b extends longitudinally through the bore 102b of the proximal connector apparatus 100b. The body of the sonic connector 130b shown in FIG. 11a is configured so as to hold the ultrasound transmission member 20b in a relatively central position within the bore 102b. Although not shown in the embodiment 100b of FIG. 11 and 11a, a tube such as tube 208 shown in FIG. 8a may be disposed about a portion of the ultrasound transmission member 20b within the body of proximal connector apparatus 100b, however, in any embodiment of the proximal connector apparatus 100, the inclusion of such tube 208 is optional and not required.

Figure 17:
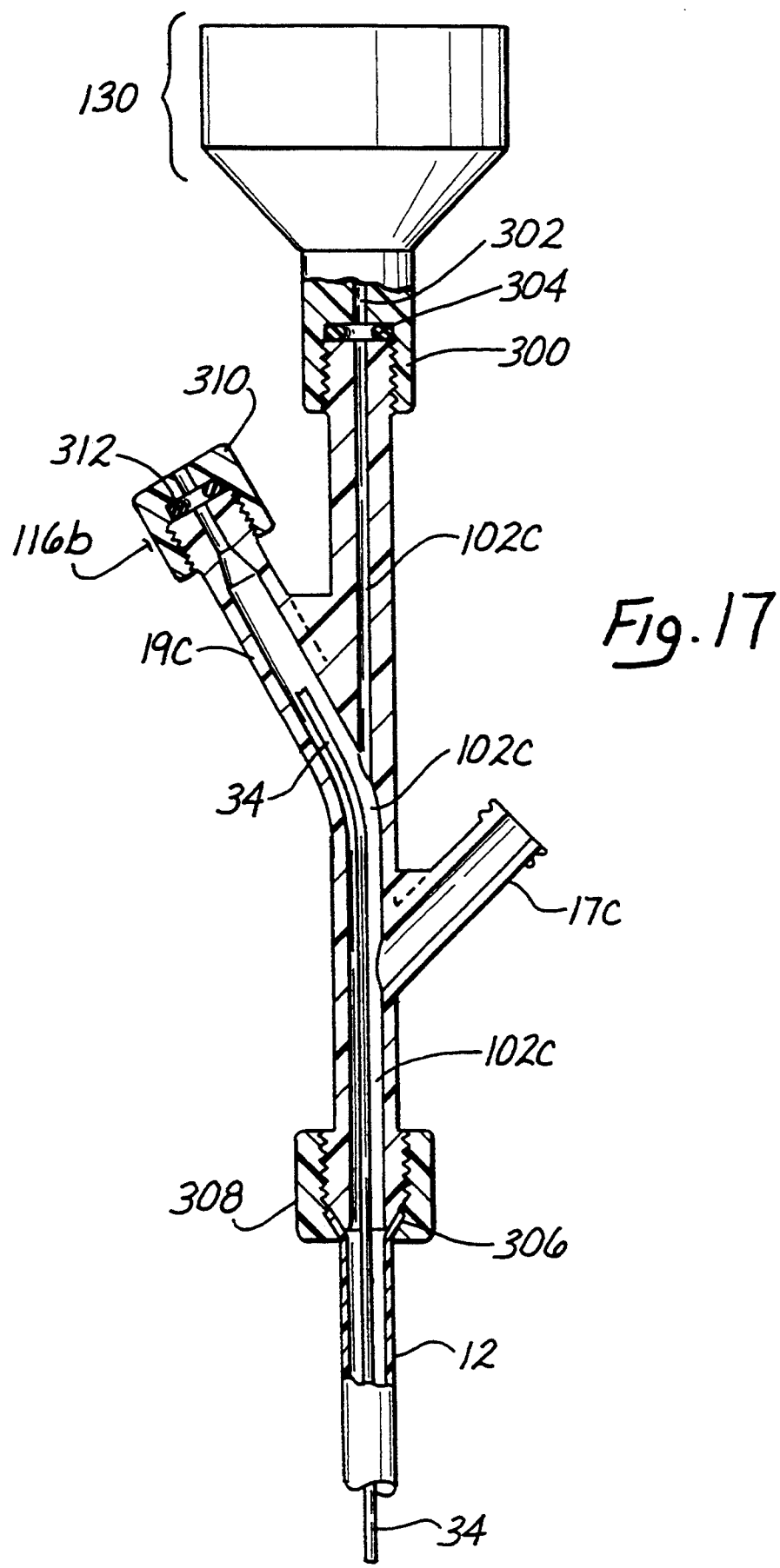
FIG. 17 is a longitudinal sectional view of an alternative embodiment of a proximal connector assembly which may be incorporated into the ultrasound catheter of the present invention.

Another alternative of the proximal connector apparatus 100 is the embodiment 100c shown in FIG. 17. FIG. 17 also includes a showing of an alternative guidewire gripping or locking apparatus 116b.

The proximal connector apparatus 100c shown in FIG. 17 comprises a single piece molded plastic body defining a hollow inner bore 102c which extends longitudinally therethrough. The hollow inner bore 102c of the embodiment shown in FIG. 17 is of larger diameter in the forward portion of the apparatus 102c as opposed to the rearward portion thereof, as shown. Such enlarged diameter of the bore 102c in the forward portion of the apparatus serves to accommodate both the ultrasound transmission member (not shown in FIG. 17) and a standard guidewire 34. The smaller diameter proximal portion of the bore 102c of the embodiment shown in FIG. 17 is slightly larger than the diameter of the ultrasound transmission member itself. Such sizing of the relatively narrow proximal portion of the bore 102c serves to hold the ultrasound transmission member in a relatively centered position within the larger diameter distal section of the bore 102c and also to prevent excessive lateral or side-to-side whipping of the ultrasound transmission member.

The sonic connector assembly 130 may be formed, configured and constructed in accordance with any embodiment of the sonic connector assembly 130 described herein. The forward or distal portion 300 of the sonic connector assembly 130 incorporated a threaded bore therein such that the sonic connector assembly 130 may be threaded onto the proximal end of the connector apparatus 102c as shown. The ultrasound transmission member lumen 302 which extends through the sonic connector apparatus 130 is thus in direct alignment with the longitudinal bore 102c of the ultrasound connector apparatus 100c. An O-ring 304 is positioned between the end of the body of the ultrasound connector apparatus 102c and the sonic connector assembly 130 threaded thereon so as to form a substantially fluid-tight seal therebetween.

A flared or diametrically expanded region 306 is formed on the proximal end of the catheter body 12 and a nut member 308 is sized, configured and constructed so as to be threadably advanced in a proximal direction over the flared region 306 upon a threaded portion formed on the distal region of the body of the proximal connector assembly 102c. When snugly threaded onto the body of the proximal connector assembly 100c, the nut member 308 forms a firm fluid-tight connection between the flared region 306 of the catheter body 12 and the proximal connector assembly 100c.

The alternative guidewire locking apparatus 116b shown in FIG. 14 comprises a threaded nut member 310 having a compressible elastomeric washer or O-ring 312 positioned therein. The O-ring is sized and formed such that as the nut member 310 is tightened down on the threads of the guidewire sidearm 19c, the O-ring 312 will flow inwardly to a point where the O-ring contacts the outer diameter of the guidewire 34, thereby holding the guidewire in fixed longitudinal position and also forming a substantially fluid tight seal around the guidewire 34. When it is desired to release the guidewire, the nut 310 is backed off slightly or loosened from its position on guidewire sidearm 19c, thereby relieving the pressure on O-ring 312, allowing O-ring 312 to relax and releasing its compressive contact with the outer diameter of the guidewire 34.

The basic sonic connector assembly 130a incorporated in the embodiment of the proximal connector apparatus 100a shown in FIG. 8a comprises a disc member 140a having a hollow frontal projection which inserts within and is affixed to the distal or rear body portion 204 of the proximal connector apparatus 100a. The disc member 140a has a concave region formed in the backside thereof, into which the ultrasound transmission member 20 inserts. A fitting is provided on the proximal end of the ultrasound transmission member 20 for connection thereof to an ultrasound transducer 24. The ultrasound transducer 24 is connected to an electrical signal generating device 25.

The concavity formed in the backside disc member 140a may be specifically shaped to lockingly hold the fitting to prevent rotation of the ultrasound transmission member 20 during use. Various alternate embodiments and configurations of the sonic connector assembly 130a are shown in FIGS. 11, 12, 13 and may be alternatively incorporated in any proximal connector apparatus 100 of the present invention. The sonic connector assembly 130b shown in FIGS. 11a and 11b comprises a disc member 140b having a first concavity 142b formed in the backside thereof and a second concavity 144b formed distal to the first concavity 142b. The second concavity 144b is sized and configured to receive the sonic connector fitting 146 therein and to prevent rotational movement of the fitting 146. The first concavity 142b forms a recessed chamber wherein the threaded proximal horn 148 will reside. The ultrasound transducer 24 is connected to the threaded proximal screw 148 as it resides within first concavity 142b.

Another alternative construction of the sonic connector assembly 130 is shown in FIGS. 12a and 12b. The sonic connector assembly 130c shown in FIGS. 12a and 12b comprises a disc member 140c having a first concavity 142c formed in the backside thereof and a second concavity 144c formed distal to the first concavity 142c. The second concavity 144c is sized and configured to receive the distal portion of the fitting 146 while the first concavity 142c is configured to receive the rectangular proximal portion of fitting 146. As shown in FIG. 12a, 12b, when operatively inserted into the device, the fitting 146 resides such that the distal portion of the fitting is inserted into the second concavity 142c while the rectangular proximal portion of the fitting 146 resides within the first concavity 144c. The shape of concavity 144c prevents rotation of the fitting 146 when operatively positioned therein.

The invention has been described herein with reference to several presently preferred embodiments. The description of and reference to these presently preferred embodiments shall not be construed as specifically limiting the invention to such presently preferred embodiments. Rather, it is intended that the invention described herein be construed as encompassing the entire scope of each of the following claims and all equivalents thereof.

We claim:

1. An ultrasonic device for removing obstructions from blood vessels, said device comprising:
   a guidewire;
   an elongate flexible catheter having a proximal end, a distal end, and a lumen extending longitudinally therethrough; an ultrasound transmission member extending longitudinally through the luemn of the flexible catheter, said ultrasonic transmission member having a distal end and a proximal end;
   a distal head formed on the distal end of said ultrasound transmission member and extending at least partially beyond the distal end of the catheter; and
   a guidewire passage aperture extending through said distal head in axial alignment with the lumen of said catheter, wherein said guidewire may be passed through said aperture and thrugh the lumen of said catheter such that said guidewire is spaced apart from said ultrasound transmission member within the lumen.

2. The device of claim 1 wherein said distal head comprises a bulbous member formed on the distal end of said ultrasound transmission member.

3. The device of claim 1 wherein said ultrasound transmission member is formed of a metal alloy.

4. The device of claim 3 wherein said metal alloy is a superelastic metal alloy.

5. The device of claim 4 wherein said superelastic metal alloy comprises a shape memory alloy capable of existing in a martensitic state and an austenitic state and which exhibits superelastic properties when in its martensitic state.

6. The device of claim 1 wherein said ultrasound transmission member is formed of nickel-titanium alloy having a nickel content of approximately 50.8 atomic percent nickel.

7. The device of claim 1 further comprising at least one coolant inlet port located near the proximal end of the catheter and at least one coolant outlet port located near the distal end of said catheter to allow a flow of coolant liquid through the lumen of the catheter in which said ultrasound transmission member is positioned.

8. The device of claim 1 further comprising a proximal connection apparatus positioned on the proximal end of said catheter, said proximal connection apparatus comprising:
   a rigid body member having a hollow inner chamber extending longitudinally therethrough, said rigid body having a proximal end and a distal end;
   the distal end of said rigid body being connected to the proximal end of said catheter such that the catheter lumen through which said ultrasound transmission member extends in fluid contact with the hollow inner chamber of said proximal connection apparatus;

said ultrasound transmission member extending through said hollow inner chamber of said proximal connector apparatus;

a sonic connector positioned on the proximal terminus of said ultrasound transmission member and connected to the proximal end of said ultrasound transmission member to permit operative connection of said ultrasound transmission member to a separate ultrasonic transducer.

9. The device of claim 8 wherein said proximal connection apparatus further comprises:

a fluid infusion aperture formed in said rigid body to permit infusion of fluid into the inner chamber of said proximal connection apparatus and through the lumen of said catheter.

10. The device of claim 9 further comprising a tubular fluid infusion sidearm having a hollow lumen in alignment with said fluid infusion aperture.

11. The device of claim 8 wherein said connection apparatus further comprises:

a guidewire exit aperture formed in said rigid body to permit passage of said guidewire out of the hollow inner chamber of said proximal connection apparatus.

12. The device of claim 11 further comprising:

a tubular guidewire exit sidearm having a hollow lumen in alignment with said guidewire exit aperture.

13. The device of claim 11 further comprising:

a guidewire diverter member insertable into said hollow inner chamber adjacent said guidewire exit aperture to divert one end of said guidewire out of said guidewire exit aperture.

14. The device of claim 13 wherein said guidewire diverter member comprises:

a tubular member having a hollow lumen extending therethrough and a beveled tip, said tubular member insertable into said guidewire exit aperture, wherein said diverter member may be rotatably moved between:

(a) a first position wherein the beveled tip of said diverter member is substantially removed from said hollow inner chamber; and a second position wherein the beveled tip of said diverter member extends at least partially into said hollow inner chamber such that said guidewire being advanced in a proximal direction through said inner chamber will be received into the lumen of said diverter member and thereby diverted out of said guidewire exit aperture through which said diverter member is inserted.

15. The device of claim 13 wherein said guidewire diverter member comprises an obturator member mounted on said rigid body and extendable into the hollow inner chamber of said proximal connection apparatus, at a location adjacent said guidewire exit aperture, to divert said guidewire out of said guidewire exit aperture.

16. The device of claim 8 further comprising:

an elongate tube member positioned around said ultrasound transmission member within the hollow inner chamber of said proximal connection apparatus to limit the side-to-side movement of said ultrasound transmission member.

17. The device of claim 1 wherein said distal head has a distal surface and wherein at least one concavity is formed in said distal surface of said distal head.

18. The device of claim 17 wherein said concavity comprises a conical depression formed in the distal surface of said distal head.

19. The device of claim 17 wherein said concavity comprises a frusto-conical depression formed in said distal surface of said distal head.

20. The device of claim 17 wherein said concavity comprises a rounded depression formed in the distal surface of said distal head.

21. The device of claim 17 wherein said guidewire passage aperture is formed at the deepest point of said concavity in the distal surface of said distal head.

22. The device of claim 1 further comprising:

a guidewire exit aperture formed at the proximal end of said flexible catheter to permit passage of said guidewire out of said flexible catheter; and means positioned on said guidewire exit aperture for locking said guidewire in a substantially fixed position relative to said catheter.

23. The device of claim 22 wherein said locking means comprises:

a tubular body insertable into said hollow inner chamber adjacent said guidewire exit aperture to divert one end of said guidewire out of said guidewire exit aperture, said tubular body having a hollow lumen extending therethrough;

gripping apparatus comprising a hollow portion through which said tubular body passes, said hollow portion having a slot extending therethrough, and said gripping apparatus having ribs provided on an outer surface; and a U-shaped slidable locking member having inner surfaces and a central tongue insertable into said slot, said tongue provided with an aperture at a central portion thereat, and a plurality of sets of grooves formed on the inner surfaces of the slidable locking member;

said aperture of said tongue aligned with said hollow lumen of said tubular body for said guidewire to extend therethrough, said ribs adapted to be seated within at least one set of said plurality of sets of grooves.

24. The device of claim 1 wherein said distal head comprises a transmission member receiving bore and wherein said distal head is mounted on said transmission member by press-fitting said transmission member into said bore without application of substantial heat to said ultrasound transmission member.

25. The device of claim 24 further comprising a heat shrink fit of said ultrasound transmission member within the bore of said distal head.

26. The device of claim 1 wherein said guidewire passage aperture comprises a chamfered enlargement at a proximal end of said guidewire passage aperture.

27. An ultrasonic device for removing obstructions from blood vessels, said device comprising:

a guidewire;

an elongate flexible catheter having a proximal end, a distal end, and at least two lumens extending longitudinally therethrough;

an ultrasound transmission member extending longitudinally through a first lumen of the flexible catheter, said ultrasonic transmission member having a distal end and a proximal end;

a distal head formed on the distal end of said ultrasound transmission member and extending at least partially beyond the distal end of the catheter;

a guidewire passage aperture extending through said distal head in axial alignment with the first lumen of said catheter, wherein said guidewire may be passed through said aperture and through a second lumen of said catheter, the first and second lumens spaced apart from each other and preventing contact of said guidewire with said ultrasound transmission member.

28. The device of claim 27, further comprising:

a guidewire exit aperture formed at the proximal end of said flexible catheter to permit passage of said guidewire out of said flexible catheter; and a guidewire diverter member insertable into said flexible catheter adjacent said guidewire exit aperture to divert one end of said guidewire out of said guidewire exit aperture.

29. The device of claim 28 wherein said guidewire diverter member comprises:

a tubular member having a hollow lumen extending therethrough and a beveled tip, said tubular member insertable into said guidewire exit aperture, wherein said diverter member may be rotatably moved between:

(a) a first position wherein the beveled tip of said diverter member is substantially removed from said flexible catheter; and (b) a second position wherein the beveled tip of said diverter member extends at least partially into said flexible catheter such that said guidewire being advanced in a proximal direction through the second lumen of said flexible catheter will be received into the hollow lumen of said diverter member and thereby diverted out of said guidewire exit aperture through which said diverter member is inserted.

30. The device of claim 28 wherein said guidewire diverter member comprises an obturator member mounted on said flexible catheter and extendable therein at a location adjacent said guidewire exit aperture, to divert said guidewire out of said guidewire exit aperture.

31. The device of claim 28 further comprising means positioned on said diverter member for locking said guidewire in a substantially fixed position relative to said catheter.

32. The device of claim 31 wherein said diverter member comprises a tubular body having a hollow lumen extending therethrough, and wherein said locking means comprises:

gripping apparatus comprising a hollow portion through which said tubular body passes, said hollow portion having a slot extending therethrough, and said gripping apparatus having ribs provided on an outer surface; and a U-shaped slidable locking member having inner surfaces and a central tongue insertable into said slot, said tongue provided with an aperture at a central portion thereat, and a plurality of sets of grooves formed on the inner surfaces of the slidable locking member;

said aperture of said tongue aligned with said hollow lumen of said tubular body for said guidewire to extend therethrough, said ribs adapted to be seated within at least one set of said plurality of sets of grooves.

33. The device of claim 28, wherein said distal head has a distal surface with at least one concavity being formed therein.

34. The device of claim 33 wherein the concavity formed in the distal surface of the distal head comprises a rounded depression.

35. The device of claim 33 wherein the concavity formed in the distal surface of the distal head comprises a conical depression.

36. The device of claim 33 wherein the concavity formed in the distal surface of the distal head comprises a frusto-conical depression.

37. An ultrasonic device for removing obstructions from blood vessels, said device comprising:

a guidewire;

an elongate flexible catheter having a proximal end, a distal end, and at least one lumen extending longitudinally therethrough;

an ultrasound transmission member extending longitudinally through a lumen of the flexible catheter, said ultrasonic transmission member having a distal end and a proximal end;

a distal head formed on the distal end of said ultrasound transmission member and extending at least partially beyond the distal end of the catheter;

a guidewire passage aperture extending through said distal head in axial alignment with a lumen of said catheter, wherein said guidewire may be passed through said aperture and through a lumen of said catheter;

a guidewire exit aperture formed at the proximal end of said flexible catheter to permit passage of a guidewire out of said flexible catheter;

a guidewire diverter member insertable into said flexible catheter adjacent said guidewire exit aperture to divert one end of said guidewire out of said guidewire exit aperture, said diverter member comprising a tubular body having a hollow lumen extending therethrough; and means positioned on said guidewire diverter member for locking said guidewire in a substantially fixed position relative to said catheter, said locking means comprising:

gripping apparatus comprising a hollow portion through which said tubular body passes, said hollow portion having a slot extending therethrough, and said gripping apparatus having ribs provided on an outer surface; and a U-shaped slidable locking member having inner surfaces and a central tongue insertable into said slot, said tongue provided with an aperture at a central portion thereat, and a plurality of sets of grooves formed on the inner surfaces of the slidable locking member;

said aperture of said tongue aligned with said hollow lumen of said tubular body for said guidewire to extend therethrough, said ribs adapted to be seated within at least one set of said plurality of sets of grooves.

38. The device of claim 37 wherein said guidewire diverter member comprises an obturator member mounted on said flexible catheter and extendable therein at a location adjacent said guidewire exit aperture, to divert said guidewire out of said guidewire exit aperture.

39. The device of claim 37 wherein said "at least one lumen" comprises a single lumen wherein said ultrasound transmission member and said flexible guidewire may both reside.

40. The device of claim 37 wherein said "at least one lumen" comprises:
   a first lumen wherein said ultrasound transmission member resides;
   and a second lumen in said guidewire passage aperture, such that said guidewire may be passed through said aperture and through said second lumen.

41. An ultrasonic device for removing obstructions from blood vessels, said device comprising:
   a guidewire;
   an elongate flexible catheter having a proximal end, a distal end, and at least one lumen extending longitudinally therethrough;
   an ultrasound transmission member extending longitudinally through the lumen of the flexible catheter, said ultrasonic transmission member having a distal end and a proximal end;
   a distal head formed on the distal end of said ultrasound transmission member and extending at least partially beyond the distal end of the catheter;
   a guidewire passage aperture extending through said distal head in axial alignment with the lumen of said catheter, wherein said guidewire may be passed through said aperture and through the lumen of said catheter;
   a guidewire exit aperture formed at the proximal end of said flexible catheter to permit passage of said guidewire out of said flexible catheter; and
   means positioned on said guidewire exit aperture for locking said guidewire in a substantially fixed position relative to said catheter, wherein said locking means comprises:
      a tubular body insertable into said hollow inner chamber adjacent said guidewire exit aperture to divert one end of said guidewire out of said guidewire exit aperture, said tubular body having a hollow lumen extending therethrough;
      gripping apparatus comprising a hollow portion through which said tubular body passes, said hollow portion having a slot extending therethrough, and said gripping apparatus having ribs provided on an outer surface; and
      a U-shaped slidable locking member having inner surfaces and a central tongue insertable into said slot, said tongue provided with an aperture at a central portion thereat, and a plurality of sets of grooves formed on the inner surfaces of the slidable locking member;
      said aperture of said tongue aligned with said hollow lumen of said tubular body for said guidewire to extend therethrough, said ribs adapted to be seated within at least one set of said plurality of sets of grooves.

42. An ultrasonic device for removing obstructions from blood vessels, said device comprising:
   a guidewire;
   an elongate flexible catheter having a proximal end, a distal end, and at least one lumen extending longitudinally therethrough;
   an ultrasound transmission member extending longitudinally through a lumen of the flexible catheter, said ultrasonic transmission member having a distal end and a proximal end;
   a distal head formed on the distal end of said ultrasound transmission member and extending at least partially beyond the distal end of the catheter;
   a guidewire passage aperture extending through said distal head in axial alignment with the first lumen of said catheter, wherein said guidewire may be passed through said aperture and through a second lumen of said catheter;
   a guidewire exit aperture formed at the proximal end of said flexible catheter to permit passage of a guidewire out of said flexible catheter; and
   a guidewire diverter member insertable into said flexible catheter adjacent said guidewire exit aperture to divert one end of said guidewire out of said guidewire exit aperture, wherein said guidewire diverter member comprises a tubular member having a hollow lumen extending therethrough and a beveled tip, said tubular member insertable into said guidewire exit aperture, wherein said diverter member may be rotatably moved between:
      (a) a first position wherein the beveled tip of said diverter member is substantially removed from said flexible catheter; and
      (b) a second position wherein the beveled tip of said diverter member extends at least partially into said flexible catheter such that said guidewire being advanced in a proximal direction through a lumen of said flexible catheter will be received into the hollow lumen of said diverter member and thereby diverted out of said guidewire exit aperture through which said diverter member is inserted.

43. An ultrasonic device for removing obstructions from blood vessels, said device comprising:
   a guidewire;
   an elongate flexible catheter having a proximal end, a distal end, and at least one lumen extending longitudinally therethrough;
   an ultrasound transmission member extending longitudinally through a lumen of the flexible catheter, said ultrasonic transmission member having a distal end and a proximal end;
   a distal head formed on the distal end of said ultrasound transmission member and extending at least partially beyond the distal end of the catheter;
   a guidewire passage aperture extending through said distal head in axial alignment with the first lumen of said catheter, wherein said guidewire may be passed through said aperture and through a second lumen of said catheter;
   a guidewire exit aperture formed at the proximal end of said flexible catheter to permit passage of a guidewire out of said flexible catheter;
   a guidewire diverter member insertable into said flexible catheter adjacent said guidewire exit aperture to divert one end of said guidewire out of said guidewire exit aperture, wherein said guidewire diverter member comprises a tubular member having a hollow lumen extending therethrough and a beveled tip, said tubular member insertable into said guidewire exit aperture, wherein said diverter member comprises a tubular body having a hollow lumen extending therethrough; and
   means positioned on said diverter member for locking said guidewire in a substantially fixed position relative to said catheter, wherein said locking means comprises:

gripping apparatus comprising a hollow portion through which said tubular body passes, said hollow portion having a slot extending therethrough, and said gripping apparatus having ribs provided on an outer surface; and a U-shaped slidable locking member having inner surfaces and a central tongue insertable into said slot, said tongue provided with an aperture at a central portion thereat, and a plurality of sets of grooves formed on the inner surfaces of the slidable locking member;

said aperture of said tongue aligned with said hollow lumen of said tubular body for said guidewire to extend therethrough, said ribs adapted to be seated within at least one set of said plurality of sets of grooves.

* * * * *